United States Patent [19]

Cooper et al.

[11] Patent Number: 5,367,052

[45] Date of Patent: Nov. 22, 1994

[54] AMYLIN PEPTIDES

[75] Inventors: Garth J. S. Cooper, Solana Beach, Calif.; Antony C. Willis, Witney, England

[73] Assignee: Amylin Pharmaceuticals, Inc., San Diego, Calif.

[21] Appl. No.: 346,624

[22] Filed: May 1, 1989

Related U.S. Application Data

[63] Continuation-in-part of Ser. No. 275,319, Nov. 23, 1988, abandoned, and a continuation-in-part of Ser. No. 236,985, Aug. 26, 1988, abandoned, said Ser. No. 275,319, is a continuation-in-part of Ser. No. 186,520, Apr. 27, 1988, abandoned.

[30] Foreign Application Priority Data

Apr. 27, 1987 [GB] United Kingdom ............. 8709871
Aug. 26, 1987 [GB] United Kingdom ............. 8720115

[51] Int. Cl.$^5$ ...................... A61K 37/02; C07K 7/10; C07K 7/36
[52] U.S. Cl. ................................. 530/307; 530/324; 530/387.9
[58] Field of Search ............... 424/85.8; 530/307, 324; 514/12

[56] References Cited

U.S. PATENT DOCUMENTS 5,112,945  5/1982  Westermark et al. ............. 530/324

OTHER PUBLICATIONS

Cooper et al., Proc. National Acad. Sci., Purification and Characterization of A Peptide from Amyloid-rich Pancreases of Type Z Diabetic Patients, Dec. 1987, pp. 8628–8632.

Westermark et al., Proc. Natl. Acad. Sci. USA, Amyloid Fibrils in Human Insulinoma and Islets of Langerhans of the Diabetic Cat are Derived from A Neuropeptide-like Protein Jun. 1987, pp. 3881–3885.

*Primary Examiner*—Lester L. Lee
*Attorney, Agent, or Firm*—Lyon & Lyon

[57] ABSTRACT

A biologically active peptide associated with diabetes and designated herein "amylin" and processes for preparing it and assaying for it and for Type 2 diabetes are disclosed. The invention includes peptides having the amino acid sequence KCNTATCATQRLANFLVHSSNNFGAILSSTNVGSNTY, substantially homologous sequences of amino acids, proamylin, as well as biologically active subfragments and conservative mutations. The peptide may be prepared from diabetic pancreata by solubilization of amyloid and isolation of the peptide by gel filtration and reverse phase chromotography. Amylin may also be synthesized, or it may be produced by recombinant DNA techniques using the disclosed nucleic acid sequences.

21 Claims, 9 Drawing Sheets

```
 1                              5                            10                             15
Lys Cys Asn Thr Ala Thr Cys Ala Thr Gln Arg Leu Ala Asn Phe 16                             20                           25                             30
Leu Val His Ser Asn Asn Phe Gly Ala Ile Leu Ser Ser Thr 31                             35
Asn Val Gly Ser Asn Thr Tyr
```

AMY1/AMY2 – derived sequence

```
K    C    N    T    A    T    C    A    T    Q
AAG  TGC  AAC  ACA  GCC  ACC  TGT  GCC  ACC  CAG

R    L    A    N    F    L    V    H    S    S
CGC  CTG  GCA  AAT  TTT  TTA  GTT  CAT  TCC  AGC

N    N    F    G    A    I    L    S    S
AAC  AAC  TTT  GGT  GCC  ATT  CTC  TCA  TCT

T    N    V    G    S    N    T    Y
ACC  AAT  GTG  GGC  TCC  AAC  ACC  ATA
```

FIG. 4.

Genomic sequence

```
TCTCAGCCAT CTAGGTGTTT GCAAACCAAA ACACTGAGTT ACTTATGTGA
         10         20         30         40         50

AAATTGTTTC TTTGGTTTTC ATCAATACAA GATATTTGAT GTCACATGGC
         60         70         80         90        100

G   S   N   F   S   H   L   F   H
TGGATCCAGC TAAAATTCTA AGG CTC TAA CTT TTC ACA TTT GTT CCA
        110        120        130                140

V   T   S   H   Q   V   E   K   R   K   C   N   T
TGT TAC CAG TCA TCA GGT GGA AAA GCG GAA ATG CAA CAC
       150            160            170            180

A   T   C   A   T   Q   R   L   A   N   F   L   V   H   S
TGC CAC ATG TGC AAC GCA GCG CCT GGC AAA TTT TTT AGT TCA TTC
       190            200            210            220        230
```

```
  S   N   N   F   G   A   I   L   S   T   N   V   G   S   N
CAG CAA CAA CTT TGG TGC CAT TCT CTC TAC CAA CGT GGG ATC CAA
        240             250             260             270

T   Y   G   K   R   N   A   V   E   V   L   K   R   E   P
TAC ATA TGG CAA GAG GAA TGC AGT AGA GGT TTT AAA GAG AGA GCC
280         290             300             310             320

L   N   Y   L   P   L   *
ACT GAA TTA CTT GCC CCT TTA GAGCA CAATCTAACT CTATAGTTAT
        330             340         350         370

TGTTTATTG TTCTAGTGAT TTCCTGTATA ATTAACAGT GCCCTTTTCA TCTCCAGTGT
            380         390         400         410         420         430

GAATATATGG TCTGTGTGTC TGATGTTTGT TGCTAGGACA TATACCTTCT CAAAAGATTG.
    440         450         460         470         480         490

TTTATATGTA GTACTAACTA AGGTCC
    500         510
```

FIG. 4 cont.

AMYLIN PEPTIDES

This application is a continuation-in-part of application Ser. No. 275,319, filed Nov. 23, 1988 and now abandoned, which is a continuation-in-part of application Ser. No. 186,520 filed Apr. 27, 1988 and now abandoned. This application is also a continuation-in-part of application Ser. No. 236,985, filed Aug. 26, 1988 and now abandoned, and incorporated herein by reference.

It appears that the accumulation of amyloid particles within the islets of Langerhans is specific for the pancreas of diabetic persons. Within the particles, one component is the peptide (previously tentatively termed "Diabetes Associated Peptide" or "DAP", and now definitively named herein "amylin").

This invention relates to peptides and in a preferred embodiment to amylin, a peptide isolatable from the pancreas of diabetics. The sequence of the peptide, which is amidated at its carboxyl terminus, is provided as are active subfragments thereof. Labeled and unlabeled substantially pure peptides are also provided, as are peptides without certain structural modifications, including a $Cys_2$-$Cys_7$ disulfide bridge and the amidation noted. This invention also relates to immunoassays for detecting the presence and amounts of such peptides, including amylin, and for detection of the most common form of diabetes, which is a particular type of diabetes mellitus (designated as Type 2 or non-insulin-dependent diabetes mellitus ("NIDDM")), which may affect more than 10% of the United States population in their late sixties (Health and Nutrition Examination Survey, Cycle II 1976–80. National Center for Health Statistics). Frequently, an unusual proteinaceous deposit is observed precipitated in the islets of Langerhans in the pancreas of such diabetic patients. The proteinaceous deposit is known as amyloid and has been previously reported (Opie E.L. *J. Exper. Med* 5:529–40 (1900) and Bell *Diabetes* 1:341344 (1952)). A nucleic acid sequence corresponding to amylin is also provided. Additionally described are processes for the isolation and purification of amylin and synthetic amylin, its synthetic production, and its production by recombinant DNA techniques using the disclosed nucleic acid sequences. Anti-amylin antibodies, monoclonal and polyclonal, labeled and unlabeled, are described as well as their various utilities, such as for use in the determination of higher levels of amylin produced in patients with Type 2 diabetes.

According to a first aspect of the present invention, there is provided a peptide which is identical to or substantially homologous with the amino acid sequence:

KCNTATCATQRLANFLVHSSNN-
FGAILSSTNVGSNTY or an active subfragment thereof.

The amino acid residues are designated by the usual single letter nomenclature. The more recent single letter designations may be correlated with the classical three letter designations of amino acid residues as follows:

| | |
|---|---|
| D = Asp | M = Met |
| E = Glu | C = Cys |
| F = Phe | L = Leu |
| K = Lys | I = Ile |
| N = Asn | H = His |
| Q = Gln | T = Thr |
| R = Arg | S = Ser |
| W = Trp | P = Pro |
| Y = Tyr | G = Gly |
| | V = Val |
| | A = Ala |

The natural peptide, whose sequence is given above, is amidated and constitutes a preferred embodiment of the invention. In addition, it is believed that in the natural peptide the cysteine residues at positions 2 and 7 cooperate to disulfide linkage. Although peptides in which the two cysteine residues do not so cooperate are within the scope of the invention, for example as preferred intermediates for the preparation of natural amylin, peptides in which the cysteine residues are linked are preferred.

Peptides in accordance with the invention may consist only of the above sequence, whether amidated or not, although the amidated peptide shows greater activity and is preferred. Alternatively, additional amino acid residues (for example one or two or even a much larger number) may be present. Additional peptides within the scope of the invention include conservative mutants of all the peptides previously mentioned. Peptides which have been post-translationally modified (e.g. glycosylated) or similarly modified by other means (especially on the S residue at position 20) are also included within the scope of the invention.

Biologically active subfragments of the above sequence are also within the scope of the invention. Such subfragments may be hexapeptides and/or may include one or more of the following sequences:

| | | | | | |
|---|---|---|---|---|---|
| KCNTAT | CATQRL | ANFLVH | SSNNFG | AILSST | NVGSNT |
| CNTATC | ATQRLA | NFLVHS | SNNFGA | ILSSTN | VGSNTY |
| NTATCA | TQRLAN | FLVHSS | NNFGAI | LSSTNV | |
| TATCAT | QRLANF | LVHSSN | NFGAIL | SSTNVG | |
| ATCATQ | RLANFL | VHSSNN | FGAILS | STNVGS | |
| TCATQR | LANFLV | HSSNNF | GAILSS | TNVGSN | |

Active subfragments may include active heptapeptides, such as one or more of the following:

| | | | | |
|---|---|---|---|---|
| KCNTATC | ATQRLAN | FLVHSSN | NFGAILS | STNVGSN |
| CNTATCA | TQRLANF | LVHSSNN | FGAILSS | TNVGSNT |
| NTATCAT | QRLANFL | VHSSNNF | GAILSST | NVGSNTY |
| TATCATQ | RLANFLV | HSSNNFG | AILSSTN | |
| ATCATQR | LANFLVH | SSNNFGA | ILSSTNV | |
| TCATQRL | ANFLVHS | SNNFGAI | LSSTNVG | |

| | | | |
|---|---|---|---|
| CATQRLA | NFLVHSS | NNFGAIL | SSTNVGS |

It is preferred that the cysteine residues at positions 2 and 7 both be present. Westermark et al. in *Biochemical and Biophysical Research Communications*, 140:827–831 (1986) give a partial description of an impure peptide deposited as amyloid fibrils in an insulin expressing tumour. They additionally state that they have some speculative evidence for its deposition in the islets of Langerhans in Type 2 Diabetes Mellitus. The sequence of the first 19 amino acids of the Westermark et al. peptide is given, but from this partial sequence it appears to be different from the peptides in accordance with the present invention as it has a serine residue at position 7. In addition, it is by no means clear that the residue at position 2 is cysteine or that the peptide as isolated is amidated.

The peptide analyzed by Westermark et. al., whatever its structure, appears to be very impure. 1.1 micrograms of material were obtained after the crude HPLC purification carried out, but only 12.2 picomoles of lysine were found after the first cycle of Edman degradation during the amino acid analysis sequence. This implies that only in the order of 30 picomoles of peptide were present in the crude extract of potentially 268 picomoles.

According to a second aspect of the present invention, there is provided substantially pure amylin or any other peptide in accordance with the first aspect. By "substantially pure" is meant purity in excess of about 50%, particularly at least about 80%, for example greater than or equal to about 90% and especially 95 or 99% by weight.

A peptide in accordance with the invention may be prepared from diabetic pancreata or synthesized. According to a third aspect of the present invention, there is provided a process for the preparation of a peptide in accordance with the first aspect, the process comprising subjecting a preparation of synthesized or solubilised amyloid first to HPLC gel filtration and secondly to reverse phase HPLC. Preferably, the reverse phase HPLC (in which the stationary phase is hydrophobic) is run immediately after the normal phase HPLC gel filtration; this helps ensure no loss of peptide in storage.

The immediate reverse phase HPLC purification step has a number of other advantages. First of all, it enables a substantially pure peptide to be isolated. Secondly, the effluent from the gel filtration is conveniently desalted. Thirdly, the peptide is concentrated to a smaller volume.

Elution of proteins by reverse phase HPLC is monitored by measuring the UV absorbance. For small peptides (those having less than about 50 amino acids), absorbance is conventionally measured at 214 nm, since small peptides may well not contain tryptophan (W) or tyrosine (Y) and therefore not absorb strongly enough at 280 nm. Reverse phase HPLC, eluting with an acetonitrile gradient and low levels of TFA (about 0.01% to about 0.5%), has been used to purify proteins. However, detection of protein peaks with higher concentrations of TFA (in the 1% range) at the UV wavelength generally used, 214 nm, has been difficult because of the interference of TFA with UV absorbance at that wavelength. However, I have found that superior separation of amylin, either radiolabeled or unlabeled, has been obtained using at least above about 0.5% TFA, preferably about 1% TFA, and monitoring elution of amylin measuring absorbance at 280 nm.

Amyloid may be solubilised in formic acid. Preferably ultrasound is used to effect or help effect solubilisation.

Amyloid is preferably obtained from the pancreas of a diabetic. The pancreas may be digested by a proteolytic enzyme such as collagenase. The pancreatic material may be prior heated (for example to 70° C.) to assist the digestion by the melting of collagen fibrils.

It appears that in the pancreas of diabetics (at least diabetics suffering from Type 2 Diabetes Mellitus), amylin is produced and deposited as amyloid. The level of production appears to be higher than the level of production in the normal (non-diabetic) pancreas. Amylin and amylin-like peptides may therefore be useful as a standard and, when detectably labelled, as a probe for use in immunoassays. According to a fourth aspect of the present invention, there is therefore provided an antigen comprising a peptide as described above. Peptides including sequences of amino acids which are different from other similar peptides may be particularly useful as antigens for specific immunoassays for amylin. For example, peptides containing residues 21 to 29 will differ from calcitonin gene related peptide ("CGRP").

According to a fifth aspect of the invention, there is also provided an antibody raised against such an antigen. This antibody could be used as a specific probe for diabetes associated peptide (amylin) and be useful for immunohistochemical or immunoassay purposes. The antibody might be used in a diagnostic test for patients who have abnormal amounts of amylin, e.g., in their plasma. In addition, when the antibody is labeled it might be used in vivo to detect the presence of amylin in amyloids in the pancreas of affected patients. It could also be used to direct a pharmaceutical agent or enzyme, eg one bound to it, which might be used to disperse the amyloid in the islets, or to inhibit growth of the amyloid. Both types of such antibodies also form part of the present invention. The antibody may be a monoclonal antibody, produced by a hybridoma. Such hybridoma cells also form part of the present invention. The antibody may also be a polyclonal antibody.

Another aspect of the present invention is directed to amylin and/or antibodies to amylin which have been labelled with an atom or group which may be readily detected and quantified. Such labelled proteins are useful in assay systems such as research assays. Means of labelling amylin or amylin antibody include radiolabelling using isotopes such as I125, $C^{14}$ or $H^3$ by using conventional methods. For example, suitable radioiodination methods include the chloramine T method (See Example 6), the iodogen method (Fraker, P. J. & Speck, J.C., *Biochem., Biophys. Res. Commun.* 80:849 (1978)), and the lactoperoxidase method (See, e.g. Marchalonis, J. J., *Biochem J.* 113:299 (1969); Hubbard, A.L. & Cohn, Z.A., *J. Cell. Biol.* 55:290 (1972); Schlager, S.I., *Methods Enzymol.* 70:252 (1980)). Other suitable radiolabelling methods include the Bolton-Hunter reagent (Bolton, A.E. & Hunter, W. M., *Biochem. J.* 133:529 (1973)) or radiolabelling by the inclusion of radiolabelled precursor amino acids in the chemical synthesis of amylin or by the inclusion of a radioisotope source in the nutrient medium of cultured cells (such as islet cells or recombinant cells). Alternatively nonradioisotopic labelling methods may be used. Such labels include those whose presence is determined either directly or indirectly. Examples of direct labels include chemiluminescent, fluorescent or spectroscopically detectable labels (See, e.g., Riggs et al. *Am. J. Pathol.* 34:1081 (1958); The, T.H. & Feltkamp, T.W.H., *Immunology* 18:865 and 875 (1970); Goding, J.W., *J. Immunol. Methods* 13:215 (1976)). Examples of indirect labels include compounds such as biotin and various antigens which can be detected by means of proteins conjugated to an appropriate detectable label (See, e.g. Bayer, E.A. & Wilchek, M., *Methods Biochem. Anal.* 26:1 (1980); Bayer, E.A. et al *FEBS Lett.* 68:240 (1976); Guesdon et. al, *J. Histochem. Cytochem.* 27:1131 (1979)). Other labelling methods include enzymes. (See, e.g. Avrameas, S. & Uriel, J., *Cr Acad. Sci. D.* 262:2543 (1966); Avrameas, S., *Histochem J.* 4:321 (1972)).

According to the above aspect of the present invention substantially pure labelled amylin and/or antibody is provided, such as purity in excess of about 50%, particularly at least about 80%, for example greater than or equal to about 90% and especially 95 or 99 percent by weight.

One preferred method of labelling the peptides of the present invention comprises labelling with radioactive iodine ($I^{125}$). Standard iodination procedures may not be suitable for use with these peptides (amylin or the C-terminal subpeptides of amylin which contain tyrosine as the C-terminal residue), since labeled peptide may be difficult to separate from the iodination mixture after iodination in normal (e.g. conventionally used) buffers. However, we have found that iodination of these peptides is possible in a 6 M guanidinium buffer, preferably of pH about 8.0 in which the buffering substance is either a phosphate buffer, preferably a 0.2 M pH 8.0 phosphate buffer, or a Tris-EDTA pH 8.0 buffer. As a result of conducting the iodination in such a buffer system, a large portion of the unbound $I^{125}$ may be separated from the radiolabeled peptide (amylin or tyrosine-containing amylin subpeptide) by gel filtration liquid chromatography in 6 M guanidine, preferably having a pH of about 8.0. The radiolabeled peptide is further purified by use of the reverse phase HPLC techniques described in Example 1. By use of these methods substantially pure (greater than about 95%) radiolabeled peptide is obtained.

The labeled peptides may be used as probes for use in single- or double-antibody immunoassays for uses such as diagnostics or as probes for ligand binding studies for use in, for example, the development of binding assays for the screening of substances which may interfere with the binding of amylin (or sub-peptides of amylin) to its receptor in order to detect candidate therapeutic substances with amylin antagonist activity.

These labeled peptides are suitable for use according to conventional immunoassay techniques based upon formation of a complex between labeled peptide (antigen) and antibody, followed by detection and/or quantitative analysis after separation of the complexed labeled antigen from uncomplexed labeled antigen.

These labeled peptides may be used according to various conventional immunoassay techniques. See, e.g., Harlow, E. and Lane, D., *Antibodies: A Laboratory Manual* (Cold Spring Harbor, New York, 1988). For example, immunoassay techniques which may be used with these radiolabeled peptides include competition immunoassay techniques wherein the antigenic substance in a sample of a fluid being tested for its presence competes with a known quantity of labeled antigen for a limited quantity of antibody binding sites. Thus, the amount of labeled antigen bound to the antibody is inversely proportional to the amount of antigen in the sample.

The labelled antibodies may be used in immunometric assays where the amount of labelled antibody associated with the complex is directly proportional to the amount of antigenic substance in the fluid sample. Various configurations known to those skilled in the art may be employed. Suitable configurations include conventional radioimmunoassays (RIA), immunoradiometric assay (IRMA), enzyme linked immunosorbent assay (ELISA), fluorescent immunoassay (FIA), immunofluorometric assay, immunoenzymatic assay and the like.

Plasma amylin levels may be measured using such immunoassays for purposes which include monitoring disease, evaluating efficacy of disease treatment such as replacement therapy or drug therapy or evaluating antagonist efficacy. Additionally, these immunoassays may be used to detect an individual's predisposition to NIDDM before the disease is manifest.

The labelled amylin and antibodies may be used in assays for the presence of anti-amylin antibodies in human disease, especially Type 1 diabetes, designated insulin-dependent diabetes mellitis ("IDDM"), and other autoimmune diseases.

The labelled anti-amylin antibodies may be used to (affinity) purify amylin or amylin-like peptides from tissues or blood using methods such as affinity chromatography. Additionally, the labelled antibodies may be used for immunohistochemistry.

Although the preparation of amylin has been demonstrated by extraction from pancreatic tissue, amylin and amylin-like peptides may be synthesized. They may also be produced by recombinant DNA techniques. The first stage in such techniques would be to obtain a length of DNA coding for amylin or an amylin-like peptide. One way to do this would be to isolate mRNA from amylin-producing cells and, with the in vitro use of reverse transcriptase produce cDNA coding for the amylin or an amylin-like peptide. Oligonucleotide probes can be produced from the known amino acid sequence and can be used to screen cDNA or genomic DNA libraries. Alternatively, given that the nucleotide sequence will generally only be just over 100 bases in length, the DNA may be chemically synthesized. A number of oligonucleotides may be produced, from which the desired cDNA can be prepared by the use of DNA polymerase and DNA ligase. Restriction endonuclease digestion of either end can leave appropriate cohesive restriction sites for insertion into a plasmid.

The genetic sequence of amylin is as listed as follows. This is a preferred embodiment, but the invention also includes conservative variations thereof, according to the genetic code.

```
5'
 K   C   N   T   A   T   C   A   T   Q   R   L   A   N   F   L
AAG TGC AAC ACA GCC ACC TGT GCC ACT CAA CGG CTG GCA AAT TTT TTA
```

```
  V   H   S   S   N   N   F   G   A   I   L   S   S   T   N   V
GTT CAT TCC AGC AAC AAC TTT GGT GCC ATT CTC TCA TCT ACC AAT GTG

3'
  G   S   N   T   Y
GGT TCC AAT ACC TAT
```

More preferred is the genetic sequence of amylin derived following isolation of the amylin gene. As set forth in Example 4 below, this sequence was derived from the genomic sequence isolated by the methods described therein, the sequence of which is shown in the attached FIG. 4.

Whether the synthetic DNA is cDNA or chemically synthesized, it can either have cohesive ends provided by a restriction endonuclease or it may be terminally tailed by for example oligo-dC by the use of the appropriate nucleotide and terminal transferase.

Whichever tailing method is chosen, a plasmid (for example pBR322) can then be taken and cleaved at a single site by a restriction endonuclease such as PstI. PstI cleaves pBR322 in the gene coding for ampicillin resistance. This allows for easy selection of recombinant plasmids. If desired, the PstI digested pBR322 can be oligo-dG tailed to complement an oligo-dC tailed piece of DNA coding for amylin or an amylin-like peptide. The cleaved plasmid and the DNA coding for amylin or an amylin-like peptide can be annealed and ligated and host cells (for example E. coli) can be transformed with amylin-containing recombinant plasmid.

The transformed E. coli host cells may be cultured under appropriate conditions to express amylin, unamidated amylin, or an amylin-like peptide.

It will therefore be seen that according to further aspects of the invention, there are provided:
- a DNA or RNA sequence coding for a peptide as described above:
- a vector (such as a plasmid) comprising such a DNA sequence; and
- a host cell (for example a bacterial cell or eukaryotic (eg yeast) cell) comprising such a vector and capable of expressing such a DNA sequence.

Amylin and other peptides and peptide preparations in accordance with the invention may also be found to have vasodilator activity, which could be either general activity or be specific for pancreas or islet blood flow. According to a further aspect of the invention, there is provided amylin or any other peptide in accordance with the first aspect for use in human or veterinary medicine. According to a still further aspect the present invention therefore provides the use of amylin or any other peptide or peptide preparation in the preparation of a vasodilator.

For a better understanding of the present invention, and to show how it may be put into effect, reference will now be made by way of example to the following experimental work and the accompanying drawings in which.

Figures 2A, 2B:
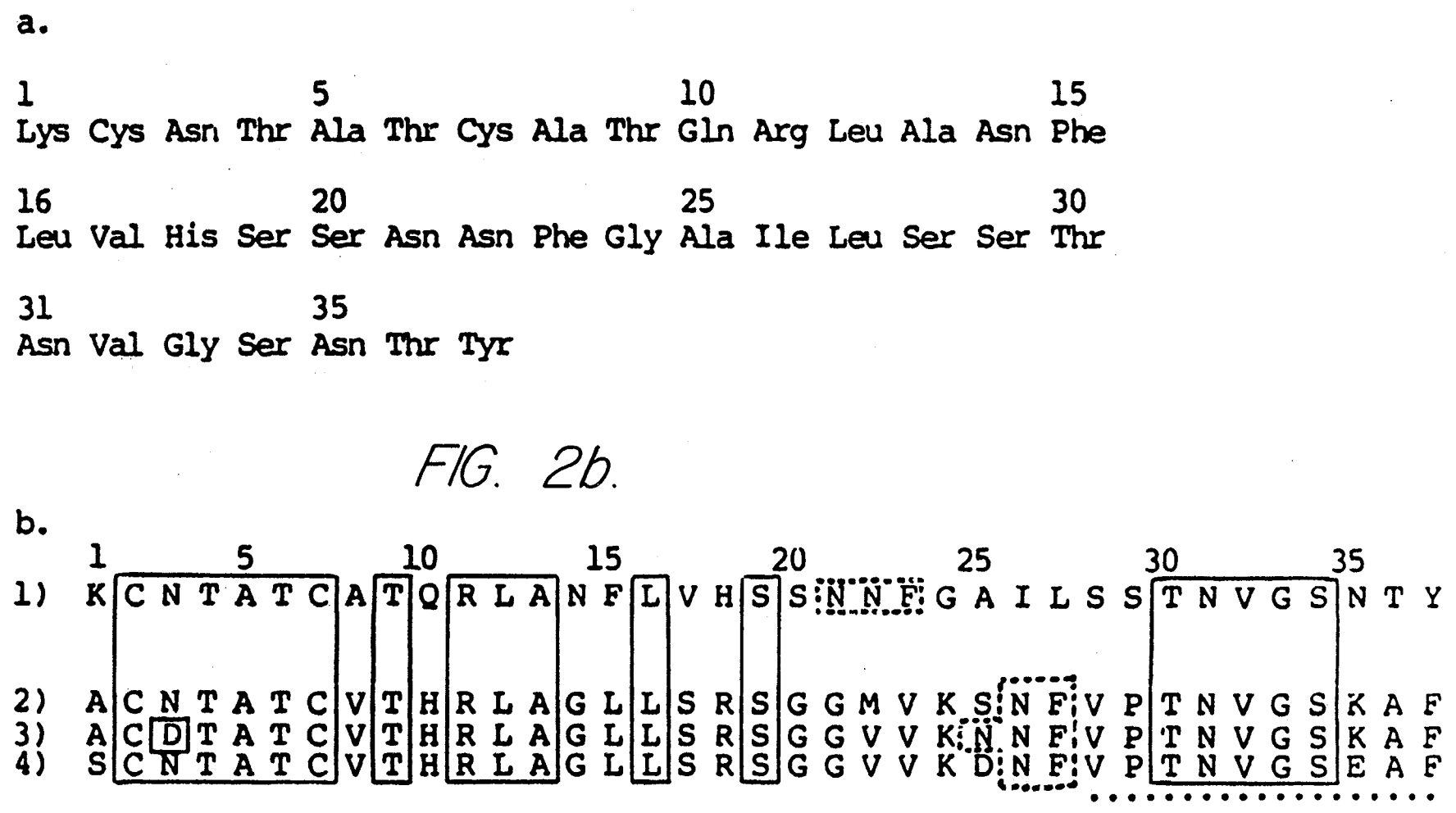
Figures 2C, 3:
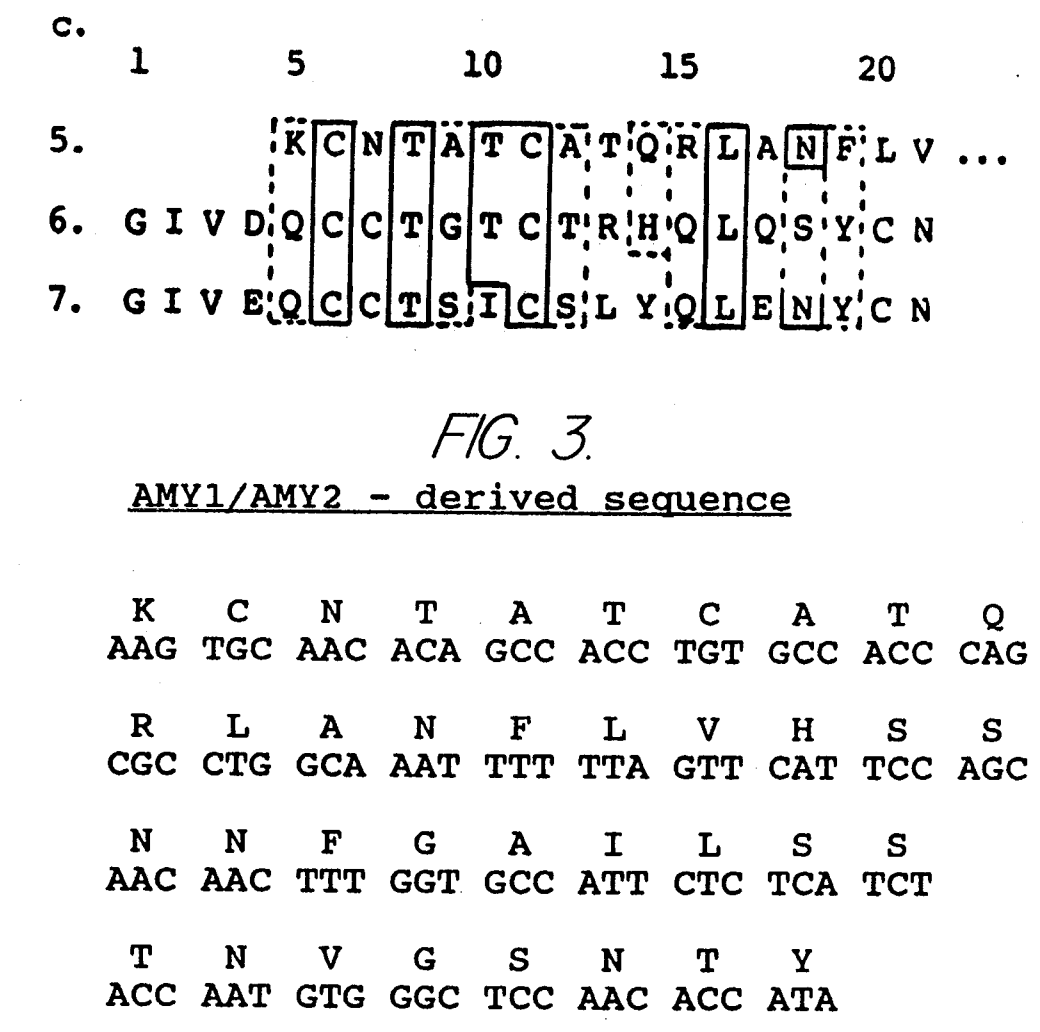
Figure 1A:
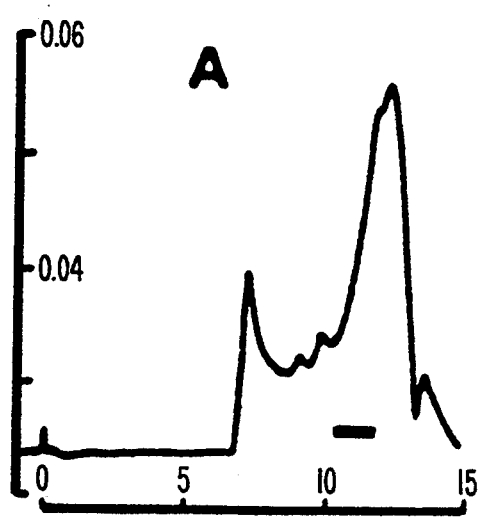
FIG. 1A shows the absorbence profile of HPLC gel filtration eluent in 6 M guanidine HC1/0.2 M sodium phosphate pH 7.5 of material derived from an amyloid containing diabetic pancreas. Amylin is present in the region shown by the bar.

FIG. 2 shows the structure of amylin (FIG. 2A), comparisons of the structure of amylin (FIG. 2B, sequence 1) as against various homologous molecules, namely, human calcitonin gene-related peptide-1 (FIG. 2B, sequence 3), human calcitonin gene-related peptide-2 (FIG. 2B, sequence 2), and rat calcitonin gene-related peptide-1 (FIG. 2B, sequence 4), and comparisons of the primary structure of amylin (FIG. 2C, sequence 5) with the alpha-chains of guinea pig insulin (FIG. 2C, sequence 6) and human insulin (FIG. 2C, sequence 7);

FIG. 3 shows the cDNA probe-derived sequence of the amylin peptide; and

Figure 5A:
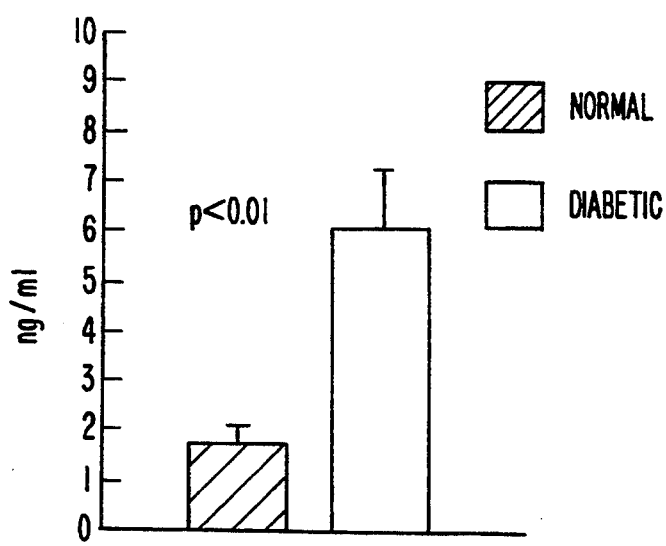
Figure 5B:
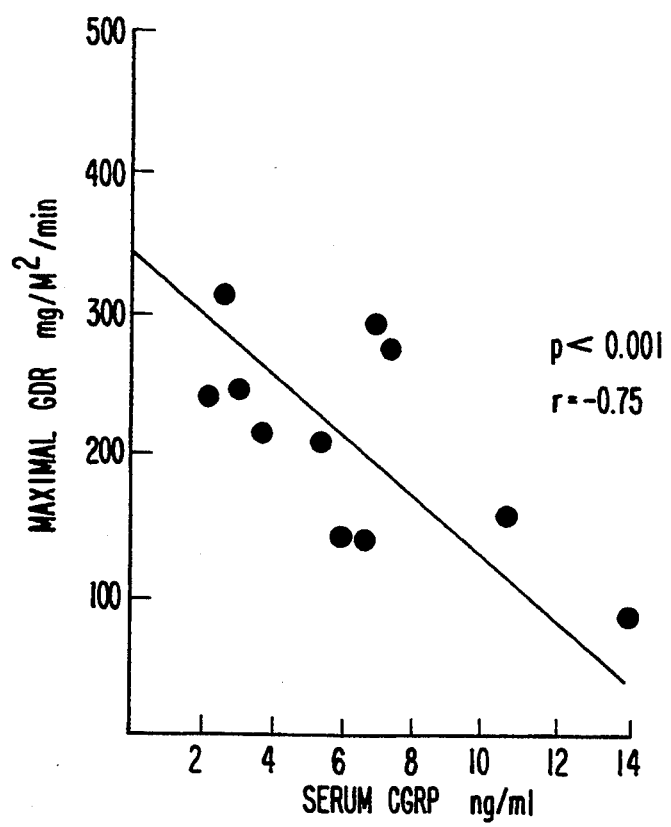

FIG. 4 shows the genomic-derived sequence including the amylin peptide, 5' intronic sequence, 3' intronic sequence, 5' and 3' KR processing signals and the 3' amidation signal/amide donor for amino acid Y;

FIG. 5A shows fasting serum CGRPLI (calcitonin gene-related peptide-like immunoreactive material) levels in control and NIDDM subjects;

FIG. 5B shows the relationship between serum CGRPLI levels and maximal insulin-stimulated glucose disposal rates in control and NIDDM subjects.

Figure 6A:
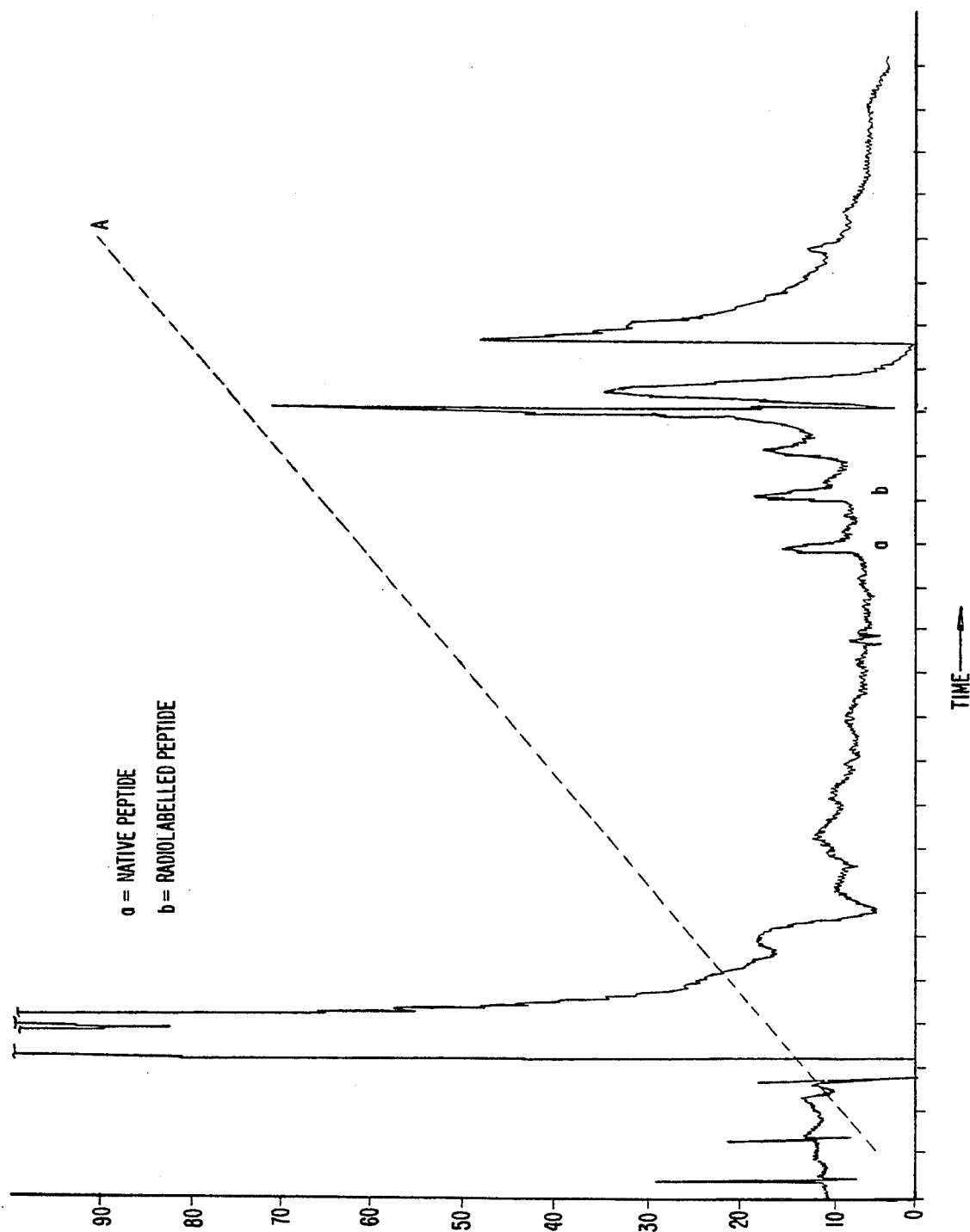

FIG. 6A shows the absorbance profile of the HPLC reverse-phase eluent of Example 6 containing radiolabeled amylin and unlabeled amylin.

Figure 6B:
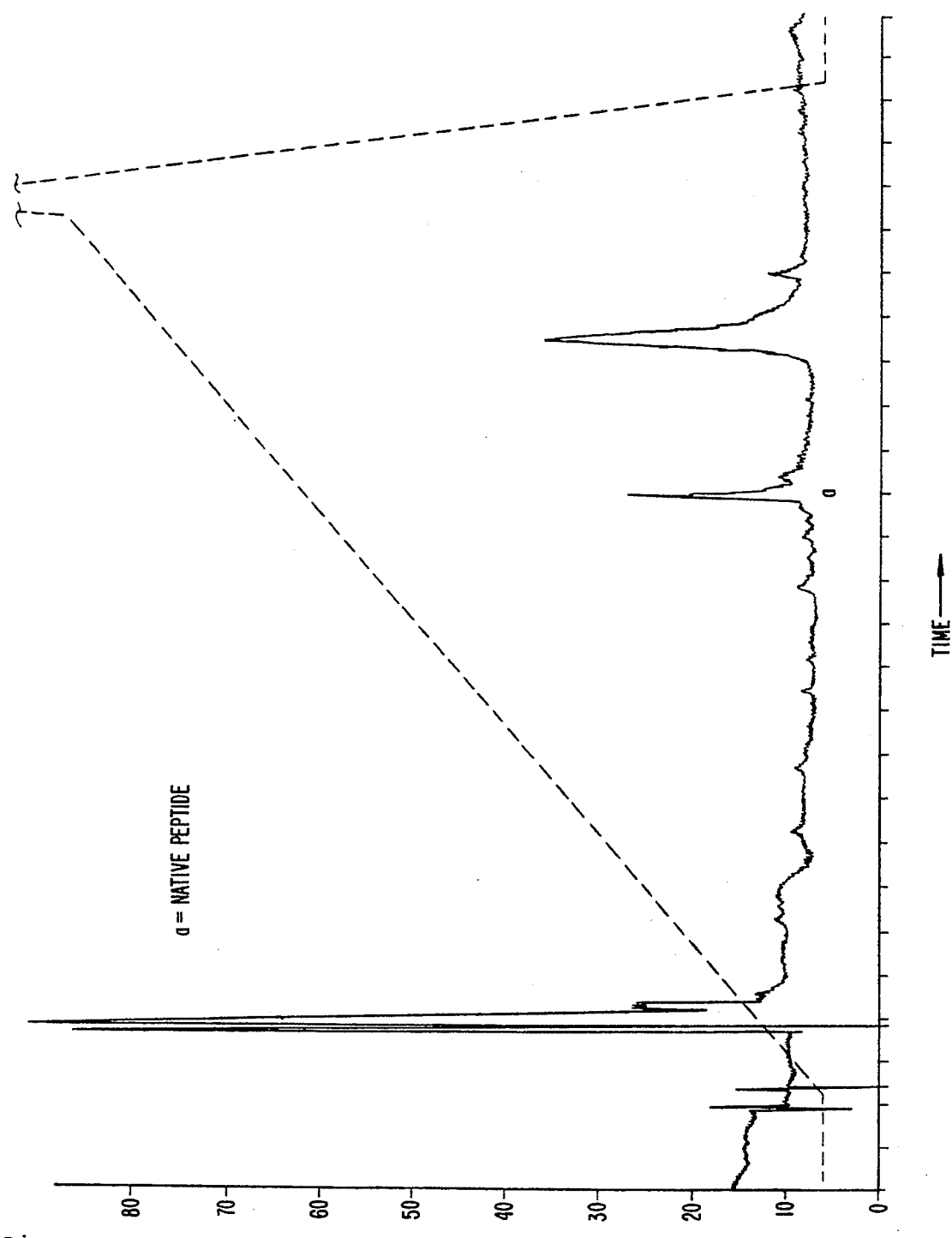

FIG. 6B depicts the HPLC reverse-phase eluent of unlabeled amylin above.

EXAMPLE 1

Pancreata from diabetics were obtained at autopsy after death and frozen at −20° C. or less until extraction. Islet amyloid was detected in tissue fixed in 150 mM NaCl/formalin 10% by light microscopy after haematoxylin and eosin staining, and confirmed after staining with alkaline Congo red by the demonstration of green birefringence by microscopy under polarized light.

Whole pancreata were homogenized in ice cold 150 mM NaCl 1:4 (w/v) and pelleted in a Sorvall RC-5B centrifuge using a GS-3 head at 10,000 g for 30 minutes at 4° C. The fat and supernatant layers were then discarded and the process was repeated twice. Crude lyophilised collagenase (EC 3.4.24.3, Boehringerher-Mannheim UK Ltd - Produce 103586) was dissolved 1:100 (w/v) in buffer, 50 mM Tris-HCl, 150 mM sodium chloride, 3 mM $CaCl_2$, (2% v/v) NONIDET-P40, pH 7.4, and purified in a Beckman LR 5B centrifuge, S.W. 40 Ti rotor at 18,000 g for 2 hours. Aliquots of the crude pancreatic homogenate were heated to 70° C. for 10 minutes and incubated with the collagenase supernate (1:10 w/v) for 20 hours at 37° C. with continuous vigorous shaking. Aliquots were pelleted in siloconised microcentrifuge tubes for 10 minutes at 11,200 g, the supernatent discarded and the procedure repeated twice with 10 volumes of 150 mM NaCl and once with 10 volumes of distilled water. Staining of aliquots with alkaline Congo red revealed 20–50% of the residue material was particles of amyloid (average diameter 10 to 30 microns), which were not seen in any of the non-diabetic, amyloid-negative control pancreata (see Example 2). The solubility of the amyloid was assessed by shaking continuously in a variety of solvents for two days, with repelleting at 11,200 g for 10 minutes, followed by microscopy after alkaline Congo red staining and protein analysis of the supernatants.

The amyloid was solubilised by ultra-sound (MSE Sonic Desintegrator, Model 150 w, wavelength 8 microns, 20 kHz) into 70% (v/v) formic acid at ¼ (w/v). Ultra-sound was delivered in four 30 second bursts with cooling in a dry ice/ethanol bath for 15 seconds after each burst. The formic acid was immediately removed by rotary evacuation to near dryness in a Sorvall SPEED VAC (Sorvall UK Ltd) and the amyloid was re-solubilised in 6 M guanidine/0.2 M sodium phosphate pH 7.5 with constant shaking for one hour.

Initial separation was achieved by high performance liquid chromatography (HPLC) gel filtration chromatography on ZORBAX GF450 and GF250 columns (250×9.4 mm DuPont (UK) Ltd) in series, in a Waters system with mobile phase 6 M guanidine/0.2 M sodium phosphate pH 7.5 and the runs were monitored at 280 nm The trace shown in FIG. 1A shows the absorbance at 280 nm.

Samples from the gel filtration system were injected directly onto a C-18 PARTISIL-10 ODS-3 reverse phase HPLC column (300×4 mm Whatman Ltd). The stationary phase was hydrophobic and PARTISIL-10 ODS-3 is the preferred particle. The mobile phase was 1% trifluoroacetic acid (TFA) with linear gradient elution by acetonitrile (5 to 80% over 45 minutes}. Runs were again monitored at 280 nm.

Figure 1B:
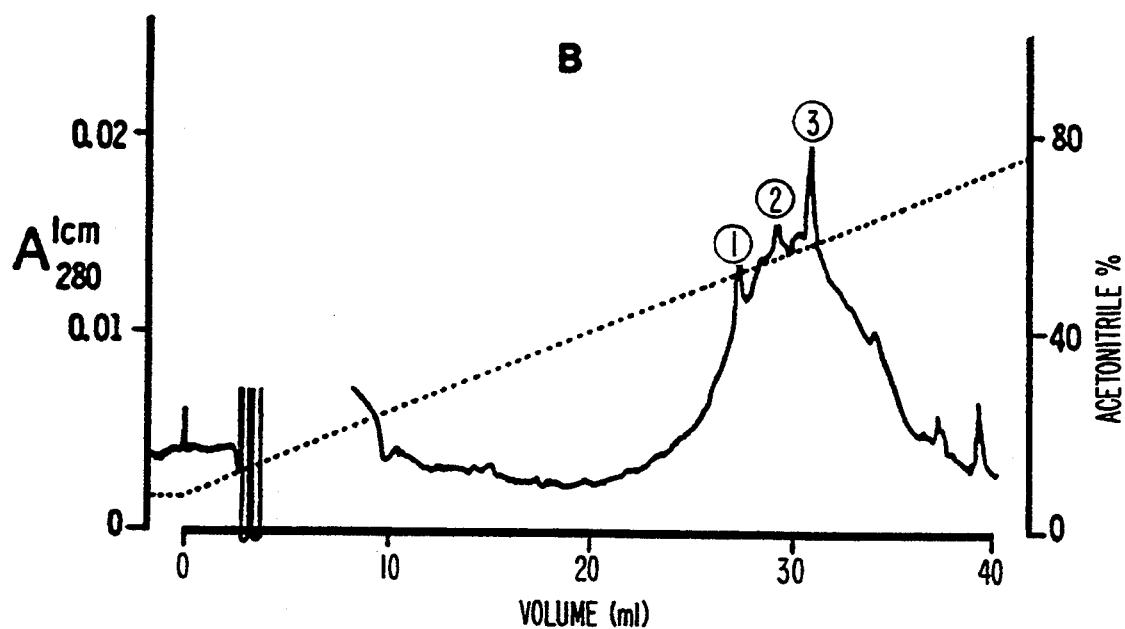
FIG. 1B, 1C and 1D show reverse phase HPLC absorbence profiles.

FIG. 1B shows the trace. Peak 3 contains native amylin. Peaks 1 and 2 appear to be contaminants, which survived the initial HPLC gel filtration purification. The elevation of baseline absorbance seen in this Figure is produced by nonproteinaceous material, which may be lipid.

Quantitative protein determination, amino acid compositions and sequence analysis were made using a Waters PICO-TAG amino acid analysis system (Cohen et al. *American Laboratory* August 1984, 48) and an Applied Biosystems 470A protein sequencer (Herrick et al. *J. Biol. Chem.* 256 (1981) 7990) using the O2CPTH cycle in the Version 2.0 software (Applied Biosystems Ltd.) Phenylthiohydatoin amino acid derivatives were identified by HPLC. The resulting sequence has been described above.

EXAMPLE 2 (COMPARISON EXAMPLE)

Figure 1C:
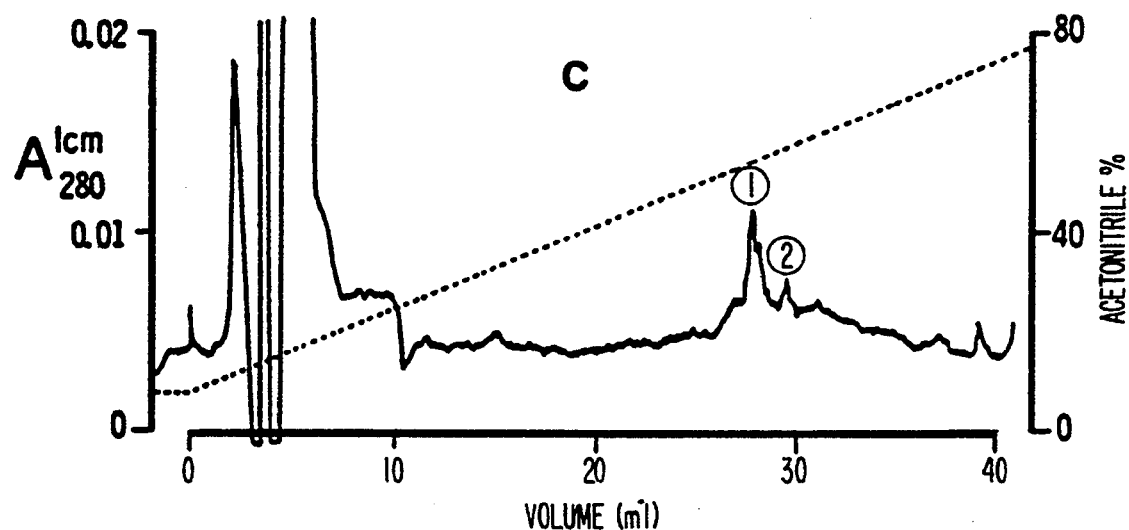

The procedure of Example 1 was repeated, except that pancreata from non-diabetics were obtained after autopsy. After collagenase digestion and pelleting, Congo red staining did not reveal any of the spherical amyloid particles. However, if the procedure was nevertheless continued to the gel filtration HPLC step, the absorbance profile was similar with the diabetic, amyloid-containing samples. This absorbance profile could therefore not be used as a guide to the presence or absence of dissolved amyloid monomer. Reinjection of a sample from the gel filtration HPLC system directly onto a reverse phase HPLC column gave rise to a reverse phase HPLC trace as shown in FIG. 1C. It can be seen that peaks corresponding to peaks 1 and 2 in FIG. 1B are present, but there is no peak corresponding to peak 3 of FIG. 1B. This peak was in fact found to be present in each of three diabetic pancreata extracted and in none of six amyloid-negative, non-diabetic control pancreata. It eluted at an acetonitrile concentration of 67.5%.

EXAMPLE 3

For the purposes of further analysis and purification, the amylin obtained in Example 1 was subjected to reduction and alkylation in the following way. Tryptic cleavage (TPCK-trypsin (Worthington UK)) of aliquots of peptide was for 3 hours at 37° C. in 100 mM ammonium bicarbonate buffer, enzyme:substrate ratio 1:100, with termination of the reaction by the addition of diisopropylfluorophosphate to 25 mM. C-terminal sequencing with carboxypeptidase Y was performed in 0.2 M pyridine-acetic acid buffer pH 5.5 with termination of reaction at 100° C. for 2 minutes. Reduction and radio S-carboxymethylation of cysteine residues were performed in 6 M guanidine/0.2 M tris pH 8.0/3 mM sodium ethylene diamine tetraacetate (EDTA) by the addition of $^{14}C$-labelled iodacetic acid (IAA) for 5 minutes, at 0° C. in the dark, followed by freshly neutralized (with 4 M NaOH) non-radio labelled IAA to 40 mM.

The thus-derivatised peptide was repurified on the same reverse phase HPLC system. It now eluted at the slightly earlier acetonitrile concentration of 64% which is consistent with the introduction of the slightly more polar carboxymethyl group into the peptide. The absorbence profile can be seen in FIG. 1D, where peak 3RA represents the derivatized peptide.

Figure 1D:
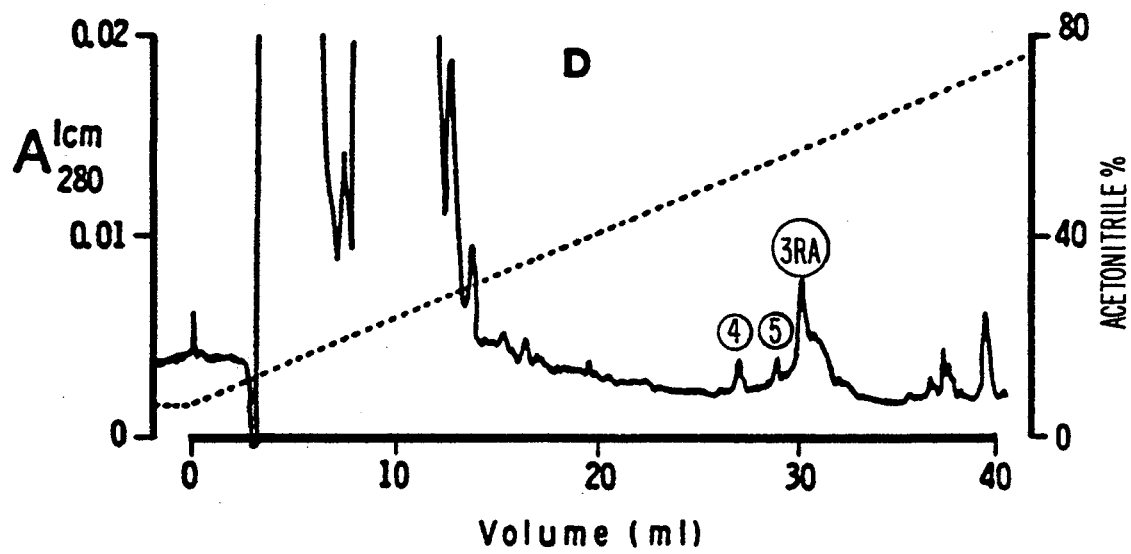

Two minor peptides, both of which had distinct amino acid analyses and both of which were amino-terminally blocked on sequence analysis, separated at this stage, and can be seen as peaks 4 and 5 in FIG. 1D. Amino acid analysis of the unpaired peak suggested the presence of a nearly-pure peptide, with a likely length of 37 amino acid residues. Its composition was distinctive, in that there was a ratio of 5 mole Asp or Asn to 1 mole Glu/Gln. This pattern was identical in the peptides purified from both of the two diabetic pancreases.

Amino acid sequence analysis gave the same results for peptides extracted from both of two diabetic pancreata. Sequence analysis was performed from both of two diabetic pancreata. Sequence analysis was also completed on native peptide after tryptic digestion, when the amino-terminal sequence was known and that after the Arg residue was determined by subtraction. From approximately 1000 pmol of pure peptide, the initial Lys residue was present at the 400 pmol level. Thereafter, on reduced and alkylated material, sequencing yields were at least 92%; however, when native material was sequenced, there was a large drop in yield at residue 2 and a second reduction at residue 7. This fact, plus the demonstration of normal yields after reduction/alkylation, suggests that the Cys residues at position 2 and 7 may form a disulphide bridge. C-terminal sequencing with CPase Y gave initially equivocal results, but also gave evidence that the C-terminal residue was Tyr.

FIG. 2A shows the structure of amylin.

FIG. 2B shows a comparison of the primary structure of native amylin (sequence 1) with the human calcitonin gene-related peptides CGRP-1 (sequence 3) and CGRP-2 (sequence 2) and rat CGRP-1 (sequence 4). The dotted boxes indicate areas of displaced homology.

FIG. 2C shows a comparison of the primary structures of amylin (sequence 5) with the alpha-chains of guinea pig insulin (sequence 6) and human insulin (sequence 7). The numbering of the residues is as for insulin. The dashed boxes represent areas of conservative amino acid substitution. Amino acid identity between peptides is indicated by boxes.

Assessment of homology by the ALIGN program and Mutation Data Matrix of Dayhoff et al. (*Methods in Enzymology* (1983) 91 524–545) gave the highly significant score of 8.31 for amylin versus human CGRP-1 (FIG. 2B, sequence 1 and sequence 3), confirming the close relationship between the two peptides. The score against the insulin alpha chain was not significant, largely because of the unmatched Cys residues at position 7 and 20 in the insulin alpha chains. Nevertheless, there is identity on three highly conserved residues in the insulin alpha chain (residues 6, 11 and 16) and a conservative change at a fourth position (Phe/Tyr at residue 19) (FIG. 2C).

EXAMPLE 4

From the sequence of the amylin polypeptide disclosed herein (see Cooper et al., *Proc Nat Acad, Sci USA* 84:8628–8632 (1987)), two oligonucleotides (AMY1 and AMY2) were designed using the human codon usage frequency table of Lathe, *J. MOl. Biol.* 183:1–12 (1985). AMY1 corresponds to the N-terminal portion of the amylin polypeptide and is equivalent to the mRNA strand; AMY2 corresponds to the unamidated C-terminal end of the amylin polypeptide and is complementary to the mRNA sequence. Both sequences are shown below:

```
      K    C    N    T    A    T    C    A    T    Q         = amylin N terminus
5' AAG TGC AAC ACA GCC ACC TGT GCC ACC CA 3'                 = AMY1

T    N    V    G    S    N    T    Y                   = amylin C terminus
5' ACC AAT GTG GGC TCC AAC ACC TA 3'
3' TGG TTA CAC CCG AGG TTG TGG AT 5'                         = AMY2
```

Total RNA was prepared from the islets of Langerhans of a beating heart organ donor by the method of Chirgwin et al., *Biochemistry* 18:5294–5299 (1979). cDNA was prepared from isolated mRNA by the method of Gubler and Hoffman, *Gene* 25:263–269 (1983) and was enhanced using Taq I polymerase with AMY1 and AMY2 as primers according to Saiki et al., *Science* (1985). The products of this enhancement were run on an agarose gel and DNA of the expected length (110 bp) was purified and re-enhanced with AMY1 and AMY2 using Klenow DNA polymerase. After purification, DNA fragments of 110 bp in length were ligated into the EcoRV site of M13mp RV8.2 (Waye et al., *Nucl. Acids Res.* (1986)), and transformed into *E. coli* JM101. Single-stranded DNA was prepared from twelve recombinant clones picked at random and sequenced. The sequence of seven out of twelve clones was the same and corresponded to a DNA sequence which encoded the central 19 amino-acids of amylin, flanked on either side by the sequence of AMY1 and AMY2. This sequence is shown in FIG. 3.

From a double-stranded DNA preparation of one of these seven clones, the insert DNA was excised with EcoRl and HindIII, subcloned into the bluescript KS(+) vector which had been cut with the same enzymes (Stratagene Cloning Systems, San Diego, Ca.), and transformed into *E. coli* TG1.

A human genomic library was prepared from the 4×cell line, GM1416B, in the vector Lambda EMBL3. The insert DNA, enhanced and cloned in the bluescript plasmid was excised with EcoRl and Hindlll, purified through an agarose gel and radio-labeled by the method of Feinberg and Vogelstein, *Anal. Biochem.* 132:6–13 (1983).

A total of approximately $10^6$ plaques of the library were screened at a density of 50000 pfu per 135 mm plate. Hybridization was carried out at 42° C. in a solution containing 50% deionized formamide/1 M NaCl/50 mM Tris-HCl 7.4/10×Denhardts (50×Denhardts=1% w/v BSA, 1% w/v PVP, 1% w/v ficoll)/0.2% w/v sodium pyrophosphate/0.1% w/v SDS and 100 ug/ml sonicated salmon sperm DNA. The filters were washed twice in 2×SSPE-0.1% SDS for 15 min at room temperature and twice in 0.5× SSPE-0.1% SDS for 30 min at 60° C. One positive clone, named Lambda EMBL-13, was identified and purified. This clone also cross-hybridized with two oligonucleotides, AMY5 (AGATGAGAGAATGGCACCAAA) and AMY6 (ACTAAAAAATTTGCCAGGCGC), which corresponded to the central portion of the isolated sequence. Restriction mapping identified a 3.0 kb Bglll fragment within Lambda EMBL-13 which cross-hybridized with the cDNA probe. This piece of DNA was subcloned into the BamHl site of pUC 118 (Vieira and Messing, *Methods Enzymol.* 153:3–11 (1987)) in both orientations (named B1 and B2). Single-stranded DNA was produced from B1 and B2 using helper phage M13K07 (id.) and sequenced initially after priming with two synthetic oligonucleotides AMY5 and AMY7 (CGCCTGGCAAATTTTTT) that corresponded to segments of the first isolated sequence.

The sequence obtained encoded polypeptide with the same sequence as amylin. Using a series of synthetic oligonucleotides as primers a DNA segment encompassing the amylin coding region was sequenced in both orientations (FIG. 4). This sequence agreed with that obtained by enhancement except for the expected differences corresponding to the "guessmer" oligonucleotides AMY1 and AMY2. From the deduced protein sequence, it was apparent that amylin is formed as a precursor protein, termed proamylin. There are basic residues (KR) at the N-terminus which are commonly found at the cleavage site of a precursor protein to active form. At the C-terminus is a 13 amino-acid chain which begins with a glycine residue, characteristic of an amidation site. Also shown are portions of 5' and 3' introns. The sequence encoding proamylin is believed to begin at nucleotide number 121.

EXAMPLE 5

Blood serum samples from control individuals and NIDDM individuals were assayed for basal levels of CGRPLI levels using polyclonal antisera raised against human CGRP. CGRP is closely homologous to amylin. Due to this close homology of amylin and CGRP, anti-CGRP antibody that cross-reacted with amylin could serve in an assay for assessing amylin levels. The use of CGRP to obtain the polyclonal antibody would be less expensive due to its commercial availability.

The control group consisted of seven males, mean age 45±4 and body mass index (BMI) 23±1 kg/m². The Type 2 group consisted of six males and five females with a mean age of 58±3 and BMI of 29±2 kg/m$^2$.

Polyclonal antisera were raised against human CGRP according to the following method:

Human CGRP having the sequence disclosed by Amara, S.G., et al., *Nature* 298:240 (1982) was synthesized by the methods of Merrifield et al. (See Barany, G. and Merrifield, R.B. in *The Peptides*, Vol. 2, pp. 1–284, (Gross, E. & Meienhofer, J., eds., Academic Press, New York, 1980)). Antibodies to conjugated CGRP were prepared using the methods described by Harlow and Lane (see Harlow, E. and Lane, D., *Antibodies: A Laboratory Manual*, pp. 72–79 (Cold Spring Harbor, New York, 1988)), and were determined to cross-react with amylin.

Fasting serum CGRPLI was measured in seven normal (control) subjects and 11 Type 2 subjects by a double antibody method with the polyclonal antisera raised against human CGRP.

CGRPLI was measured by radioimmunoassay procedures (see Yalow, R.S. & Berson, S.A., *Nature* 184:1648 (1959)), using anti-CGRP antibodies prepared as noted above and radiolabeled CGRP. Positive controls using CGRP and amylin were also established.

Mean serum CGRPLI levels for the control and NIDDM subjects are shown in FIG. 5A.

Steady state glucose disposal rates (mg/M$^2$/min) were measured isotopically with 3-$^3$H-glucose during hyperinsulinemic euglycemic clamp studies in the seven controls and 11 NIDDM subjects at a maximally stimulating serum insulin concentration (1160±67 uU/ml) as described in Olefsky, J.M. et al., *Am. J. Med.* 70:151 (1981). The relationship between serum CGRPLI levels and maximal insulin-stimulated disposal rates in the control and NIDDM is shown in FIG. 5B, and was shown to have a correlation coefficient of −0.75, p>0.001.

The results set forth show a strong correlation (r=−0.75, p<0.001) between the severity of insulin resistance in the Type 2 diabetic subjects, as measured by the determination of maximal insulin-stimulating glucose uptake and the levels of CGRPLI in the blood. As the degree of insulin resistance is an excellent measure of the severity of the Type 2 diabetic state, these data demonstrate the relationship between levels of CGRPLI in the blood of Type 2 diabetics and the severity of the disease state. The variance inherent in these results (var=r$^2$=0.58), provides further support for this relationship. It also supports our conclusion of a causal relationship between blood levels of CGRPLI and insulin resistance in Type 2 diabetes mellitus and, of course, supports our early conclusions with regard to amylin and CGRP and Type 2 diabetes mellitus.

EXAMPLE 6

Amylin was radioiodinated using I$^{125}$ for use in a radioimmunoassay.

Amylin (20 mg of amylin 7–37) was iodinated by the chloramine-T method (See, e.g., Hunter, W. M. et al, *Nature* 194:495 (1962); Greenwood et al., *Biochem. J.* 89:114 (1963); McConaghy et al, *Methods Enzymol.* 7.0:210 (1980)) in a 6 M guanidine buffer. A large portion of unbound I$^{125}$ was separated from the radiolabeled amylin by gel filtration liquid chromatography in 6 M guanidine. Labeled peptide was separated from unlabeled peptide and from remaining free radioiodine by use of the 1% TFA/(5–95% acetonitrile 45 min.) reverse-phase HPLC system described in Example 1.

FIG. 6A shows the result of the reverse phase chromatography of the radiolabeled peptide, illustrating separation of radiolabeled peptide from residual non-radiolabeled peptide and free radioiodine. FIG. 6B, for comparison, is a chromatograph of unlabeled peptide and shows only one peak. The labeled peak is identified by comparing FIGS. 6A and 6B; the identification is confirmed by counting the samples using a liquid scintillation counter after drying down the samples.

I claim:

1. An amylin peptide having thirty-seven amino acids, in which the C-terminal tyrosine of said peptide is carboxyamidated, said peptide contains an intramolecular linkage between cysteine resides at positions 2 and 7, and wherein said peptide is capable of reducing insulin-induced incorporation of glucose into glycogen in isolated rat soleus muscle.

2. The amylin peptide KCNTATCATQRLANFLVHSSNNFGAILSSTNVGSNTY which contains an intramolecular linkage between the cysteine residues at positions 2 and 7, and wherein the C-terminal tyrosine is carboxyamidated.

3. A process for the preparation of an amylin peptide as recited in claim 2, comprising the steps of (a) preparing solubilized amyloid by use of formic acid in conjunction with ultrasound, (b) subjecting the amyloid material from step (a) to normal phase high performance liquid chromatography gel filtration using a mobile phase comprising aqueous guanidine and sodium phosphate, and (c) subjecting the amyloid material from step (b) to high performance liquid chromatography using a mobile phase comprising triflouracetic acid and elution by acetonitrile.

4. A substantially pure amylin peptide prepared by the process of claim 3.

5. An amylin peptide as recited in claim 1 or 2 which is at least about 50% pure.

6. An amylin peptide as recited in claim 1 or 2 which is at least about 80% pure.

7. An amylin peptide as recited in claim 1 or 2 which is at least about 90% pure.

8. An amylin peptide as recited in claim 1 or 2 which is at least about 95% pure.

9. An amylin peptide as recited in claim 1 or 2 which is at least about 99% pure.

10. The amylin peptide of claim 4 wherein said amylin peptide is an amylin peptide having thirty-seven amino acids, in which the C-terminal tyrosine of said peptide is carboxyamidated. said peptide contains an intramolecular linkage between the cysteine residues at positions 2 and 7, and wherein said peptide is capable of reducing insulin-induced incorporation of glucose into glycogen in isolated rat soleus muscle.

11. The amylin peptide of claim 5 wherein said amylin peptide is an amylin peptide having thirty-seven amino acids, in which the C-terminal tyrosine of said peptide is carboxyamidated, said peptide contains an intramolecular linkage between the cysteine residues at positions 2 and 7, and wherein said peptide is capable of reducing insulin-induced incorporation of glucose into glycogen in isolated rat soleus muscle.

12. The amylin peptide of claim 6 wherein said amylin peptide is an amylin peptide having thirty-seven amino acids, in which the C-terminal tyrosine of said peptide is carboxyamidated, said peptide contains an intramolecular linkage between the cysteine residues at positions 2 and 7, and wherein said peptide is capable of reducing insulin-induced incorporation of glucose into glycogen in isolated rat soleus muscle.

13. The amylin peptide of claim 7 wherein said amylin peptide is an amylin peptide havng thirty-seven amino acids, in which the C-terminal tyrosine of said peptide is carboxyamidated, said peptide contains an intramolecular linkage between the cysteine residues at positions 2 and 7, and wherein said peptide is cabable of reducing insulin-induced incorporation of glucose into glycogen in isolated rat soleus muscle.

14. The amylin peptide of claim 8 wherein said amylin peptide is an amylin peptide having thirty-seven amino acids, in which the C-terminal tyrosine of said peptide is carboxyamidated, said peptide contains an intramolecular linkage between the cysteine residues at positions 2 and 7, and wherein said peptide is capable of reducing insulin-induced incorporation of glucose into glycogen in isolated rat soleus muscle.

15. The amylin peptide of claim 9 wherein said amylin peptide is an amylin peptide having thirty-seven amino acids, in which the C-terminal tyrosine of said peptide is carboxyamidated, said peptide contains an intramolecular linkage between the cysteine residues at positions 2 and 7, and wherein said peptide is capable of reducing insulin-induced incorporation of glucose into glycogen in isolated rat soleus muscle.

16. The amylin peptide of claim 4 wherein said amylin peptide is the amylin peptide KCNTATCATQRLANFLVHSSNNFGAILSSTNVGSNTY which contains an intramolecular linkage between the cysteine residues at positions 2 and 7, and wherein the C-terminal tyrosine is carboxyamidated.

17. The amylin peptide of claim 5 wherein said amylin peptide is the amylin peptide KCNTATCATQRLANFLVHSSNNFGAILSSTNVGSNTY which contains an intramolecular linkage between the cysteine residues at positions 2 and 7, and wherein the C-terminal tyrosine is carboxyamidated.

18. The amylin peptide of claim 6 wherein said amylin peptide is the amylin peptide KCNTATCATQRLANFLVHSSNNFGAILSSTNVGSNTY which contains an intramolecular linkage between the cysteine residues at positions 2 and 7, wherein the C-terminal tyrosine is carboxyamidated.

19. The amylin peptide of claim 7 wherein said amylin peptide is the amylin peptide KCNTATCATQRLANFLVHSSNNFGAILSSTNVGSNTY which contains an intramolecular linkage between the cysteine residues at positions 2 and 7, wherein the C-terminal tyrosine is carboxyamidated.

20. The amylin peptide of claim 8 wherein said amylin peptide is the amylin peptide KCNTATCATQRLANFLVHSSNNFGAILSSTNVGSNTY which contains an intramolecular linkage between the cysteine residues at positions 2 and 7, wherein the C-terminal tyrosine is carboxyamidated.

21. The amylin peptide of claim 9 wherein said amylin peptide is the amylin peptide KCNTATCATQRLANFLVHSSNNFGAILSSTNVGSNTY which contains an intramolecular linkage between the cysteine residues at positions 2 and 7, wherein the C-terminal tyrosine is carboxyamidated.

* * * * *